(12) United States Patent
Qadir et al.

(10) Patent No.: US 12,183,105 B2
(45) Date of Patent: Dec. 31, 2024

(54) METHOD TO IMPROVE INSTANCE SELECTION IN BOOTSTRAPPING FRAMEWORK FOR CONCEPT EXTRACTION FROM TEXT DOCUMENTS

(71) Applicant: KONINKLIJKE PHILIPS N.V., Eindhoven (NL)

(72) Inventors: Ashequl Qadir, Melrose, MA (US); Kathy Mi Young Lee, Westford, MA (US); Claire Yunzhu Zhao, Boston, MA (US); Aaditya Prakash, Waltham, MA (US); Minnan Xu, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 373 days.

(21) Appl. No.: 17/781,074

(22) PCT Filed: Dec. 18, 2020

(86) PCT No.: PCT/EP2020/086913
§ 371 (c)(1),
(2) Date: May 31, 2022

(87) PCT Pub. No.: WO2021/123083
PCT Pub. Date: Jun. 24, 2021

(65) Prior Publication Data
US 2023/0015207 A1    Jan. 19, 2023

Related U.S. Application Data

(60) Provisional application No. 62/949,824, filed on Dec. 18, 2019.

(51) Int. Cl.
*G06V 30/413*    (2022.01)
*G06V 10/774*    (2022.01)
(Continued)

(52) U.S. Cl.
CPC .......... *G06V 30/413* (2022.01); *G06V 10/774* (2022.01); *G16H 15/00* (2018.01); *G16H 30/40* (2018.01)

(58) Field of Classification Search
None
See application file for complete search history.

(56) References Cited

U.S. PATENT DOCUMENTS

2018/0165554 A1 *   6/2018   Zhang .................... G06N 3/045
2019/0205733 A1      7/2019   Ghaenini
(Continued)

FOREIGN PATENT DOCUMENTS

WO    WO2018042211 A1    3/2018
WO    WO2019051359 A1    3/2019

OTHER PUBLICATIONS

PCT International Search Report, International application No. PCT/EP2020/086913, Mar. 24, 2021.
(Continued)

*Primary Examiner* — Dov Popovici

(57) ABSTRACT

A system and method for unsupervised training of a text report identification machine learning model, including: labeling a first set of unlabeled text reports using a seed dictionary to identify concepts in the unlabeled text reports; inputting images associated with the first set of seed-labeled text reports into an auto-encoder to obtain an encoded first set of images; calculating a set of first correlation matrices as a dot product of the first encoded images with their associated text report features; determining a distance between the set of first correlation matrices and a filter bank value associated with the auto-encoder; identifying a first set of validated images as the images in the first set of images that have a distance less than a threshold value; and training
(Continued)

the text report machine learning model using the labeled text reports associated with the set of first validated images.

16 Claims, 5 Drawing Sheets

(51) Int. Cl.
*G16H 15/00* (2018.01)
*G16H 30/40* (2018.01)

(56) References Cited

U.S. PATENT DOCUMENTS

2021/0065859 A1* 3/2021 McKinney ............. G16H 30/40
2023/0005252 A1* 1/2023 Qadir ................ G06V 10/7747

OTHER PUBLICATIONS

Chaochao Yan et al., "Weakly Supervised Deep Learning for Thoracic Disease Classification and Localization on Chest X-Rays", arxiv.org, Cornell University Library, 201 Olin Library Cornell University Ithaca, NY 14853, Jul. 16, 2018 (Jul. 16, 2018), XP081113044.

Cornegruta S. et al., "Modelling Radiological Language with Bidirectional Long Short-Term Memory Networks", arXiv preprint arXiv:1609.08409 (2016).

Zhiheng H. et al., "Bidirectional LSTM-CRF Models for Sequence Tagging", arXiv preprint arXiv:1508.01991, 2015.

Haug P.J. et al., "Computerized Extraction of Coded Findings from Free-Text Radiologic Reports. Work in Progress", vol. 174, issue 2, pp. 543-548, Feb. 1990. https://pubs.rsna.org/doi/abs/10.1148/radiology.174.2.2404321.

Elkin P. L. et al., "NLP-Based Identification of Pneumonia Cases from Free-Text Radiological Reports", Journal List AMIA Annual Symposium Proceedings, Nov. 6, 2008;2008:172-6. https://www.ncbi.nlm.nih.gov/pmc/articles/PMC2656026/.

Hazen R. et al., "Automatic Extraction of Concepts to Extend RadLex", Journal of Digital Imaging, vol. 24 Issue 1, pp. 165-169, 2011. https://link.springer.com/article/10.1007/s10278-010-9334-1.

Reed S.E. et al., "Training Deep Neural Networks on Noisy Labels with Bootstrapping", Computer Vision and Pattern Recognition (cs.CV); Machine Learning (cs.LG); Neural and Evolutionary Computing (cs.NE), 2015. https://arxiv.org/pdf/1412.6596.pdf.

\* cited by examiner

METHOD TO IMPROVE INSTANCE SELECTION IN BOOTSTRAPPING FRAMEWORK FOR CONCEPT EXTRACTION FROM TEXT DOCUMENTS

CROSS-REFERENCE TO PRIOR APPLICATIONS

This application is the U.S. National Phase application under 35 U.S.C. § 371 of International Application No. PCT/EP2020/086913, filed on Dec. 18, 2020, which claims the benefit of U.S. Provisional Application Ser. No. 62/949,824, filed on Dec. 18, 2019. These applications are hereby incorporated by reference herein.

TECHNICAL FIELD

Various exemplary embodiments disclosed herein relate generally to a method to improve instance selection in bootstrapping framework for concept extraction from text documents.

BACKGROUND

Being able to automatically identify important concepts (e.g., disease/symptom, anatomy, severity in clinical notes) in text is important to allow learning of computational models that can understand the information conveyed in unstructured text data. In some scenarios, the text data from which the concepts need to be identified may be accompanied by images containing similar and/or complementary information. For example, several types of clinical notes such as X-ray, Ultrasound or MRI reports originate from medical images where the images are narrated by a medical professional (e.g., a radiologist) for the benefit of the ordering physician or for documenting the current state of a patient as observed in the images. Traditional natural language processing-based information extraction systems primarily work on the text data and do not take advantage of the accompanying images when such images are available.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a method for weakly-supervised training of a text report identification machine learning model, including: labeling a first set of unlabeled text reports using a seed dictionary to identify concepts in the unlabeled text reports; inputting images associated with the first set of seed-labeled text reports into an auto-encoder to obtain an encoded first set of images; calculating a set of first correlation matrices as a dot product of the first encoded images with their associated text report features; determining a distance between the set of first correlation matrices and a filter bank value associated with the auto-encoder; identifying a first set of validated images as the images in the first set of images that have a distance less than a threshold value; and training the text report machine learning model using the labeled text reports associated with the set of first validated images.

Various embodiments are described, further including labeling a second set of unlabeled text reports using trained text report machine learning model; inputting images associated with the second set newly-labeled text reports into an auto-encoder to obtain an encoded second set of images; calculating a set of second correlation matrices as a dot product of the second encoded images with their associated text report features; determining a distance between the set of second correlation matrices and the filter bank value associated with the auto-encoder; identifying a second set of validated images as the images in the second set of images that have a distance less than a threshold value; and training the text report machine learning model using the labeled text reports associated with the first set of validated images and second set of validated images.

Various embodiments are described, further including repeating the step of claim 2 with additional sets of unlabeled data.

Various embodiments are described, further including completing training text identification machine learning model when no further unlabeled data is available.

Various embodiments are described, further including determining the performance of the text identification model using a validation set of data for each iteration of claim 3.

Various embodiments are described, further including completing training text identification machine learning model when the performance between iterations is less than a performance change threshold value.

Various embodiments are described, further including training the auto-encoder using a loss function based upon the error between an input and output image of the auto-encoder and the correlation matrix.

Various embodiments are described, wherein the loss function is calculated as:

$$J = MSE - \lambda I'^T \cdot T,$$

where J is the loss function, MSE is the mean square error between the input image and output image of the auto-encoder, $\lambda$ is a hyperparameter, $I'^T \cdot T$ is a correlation matrix, $I'^T$ is the transpose of the encoded image, and T is the text report features.

Further various embodiments relate to a system for training a text report identification machine learning model and an image identification machine learning model, including: a memory; a processor connected to the memory, the processor configured to: label a first set of unlabeled text reports using a seed dictionary to identify concepts in the unlabeled text reports; input images associated with the first set of seed-labeled text reports into an auto-encoder to obtain an encoded first set of images; calculate a set of first correlation matrices as a dot product of the first encoded images with their associated text report features; determine a distance between the set of first correlation matrices and a filter bank value associated with the auto-encoder, identify a first set of validated images as the images in the first set of images that have a distance less than a threshold value; and train the text report machine learning model using the labeled text reports associated with the set of first validated images.

Various embodiments are described, wherein the processor is further configured to: label a second set of unlabeled text reports using trained text report machine learning model; input images associated with the second set of newly-labeled text reports into an auto-encoder to obtain an encoded second set of images; calculate a set of second correlation matrices as a dot product of the second encoded images with their associated text report features; determine a distance between the set of second correlation matrices and the filter bank value associated with the auto-encoder, identify a second set of validated images as the images in the second set of images that have a distance less than a threshold value; and train the text report machine learning model using the labeled text reports associated with the first set of validated images and second set of validated images.

Various embodiments are described, wherein the processor is further configured to: repeat the steps of claim 10 with additional sets of unlabeled data.

Various embodiments are described, wherein the processor is further configured to complete training text identification machine learning model when no further unlabeled data is available.

Various embodiments are described, wherein the processor is further configured to determine the performance of the text identification model using a validation set of data for each iteration of claim 11.

Various embodiments are described, wherein the processor is further configured to complete training text identification machine learning model when the performance change between iterations is less than a performance threshold value.

Various embodiments are described, wherein the processor is further configured to train the auto-encoder using a loss function based upon the error between an input and output image of the auto-encoder and the correlation matrix.

Various embodiments are described, wherein the loss function is calculated as:

$$J = MSE - \lambda I'^T \cdot T,$$

where J is the loss function, MSE is the mean square error between the input image and output image of the auto-encoder, $\lambda$ is a hyperparameter, $I'^T \cdot T$ is a correlation matrix, $I'^T$ is the transpose of the encoded image, and T is the text report features.

BRIEF DESCRIPTION OF THE DRAWINGS

In order to better understand various exemplary embodiments, reference is made to the accompanying drawings, wherein.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Embodiments of a bootstrapping training system are described using a weakly supervised bootstrapping framework that is capable of additionally utilizing the images accompanying text reports for improving concept extraction from the text reports. The images are used to validate and select a sample set of supplemental training instances for a target concept found in the text reports which will better represent the target concept and thus allow for less noise in supplemental training data for that concept in the iterative semi-supervised learning paradigm. Applications in the medical domain for the extracted concepts (e.g., from clinical notes) can benefit downstream algorithms such as prompt recognition of heart failure patients or facilitating emergency department (ED) disposition and triaging algorithms.

One of the major limitations of supervised information extraction systems is that they require labeled training data which are scarce. In the medical domain, it is particularly costly to acquire labeled medical concepts in clinical notes because the annotations need to be done by highly skilled medical professionals such as radiologists. This problem can be addressed with bootstrapped learning that allows iteratively increasing an initial small collection of labeled training data with supplemental training data that are automatically labeled from a large collection of unlabeled data. However, in the self-training paradigm, where the learning algorithm self identifies new supplemental data, such an approach propagates noise in successive iterations. Embodiments of a bootsrapping training system implementing a bootstrapping framework will be described that address this problem by additionally leveraging images of the identified instances to select higher quality supplemental training data, thus resulting in more effective concept extraction ability from text data.

Figure 1:
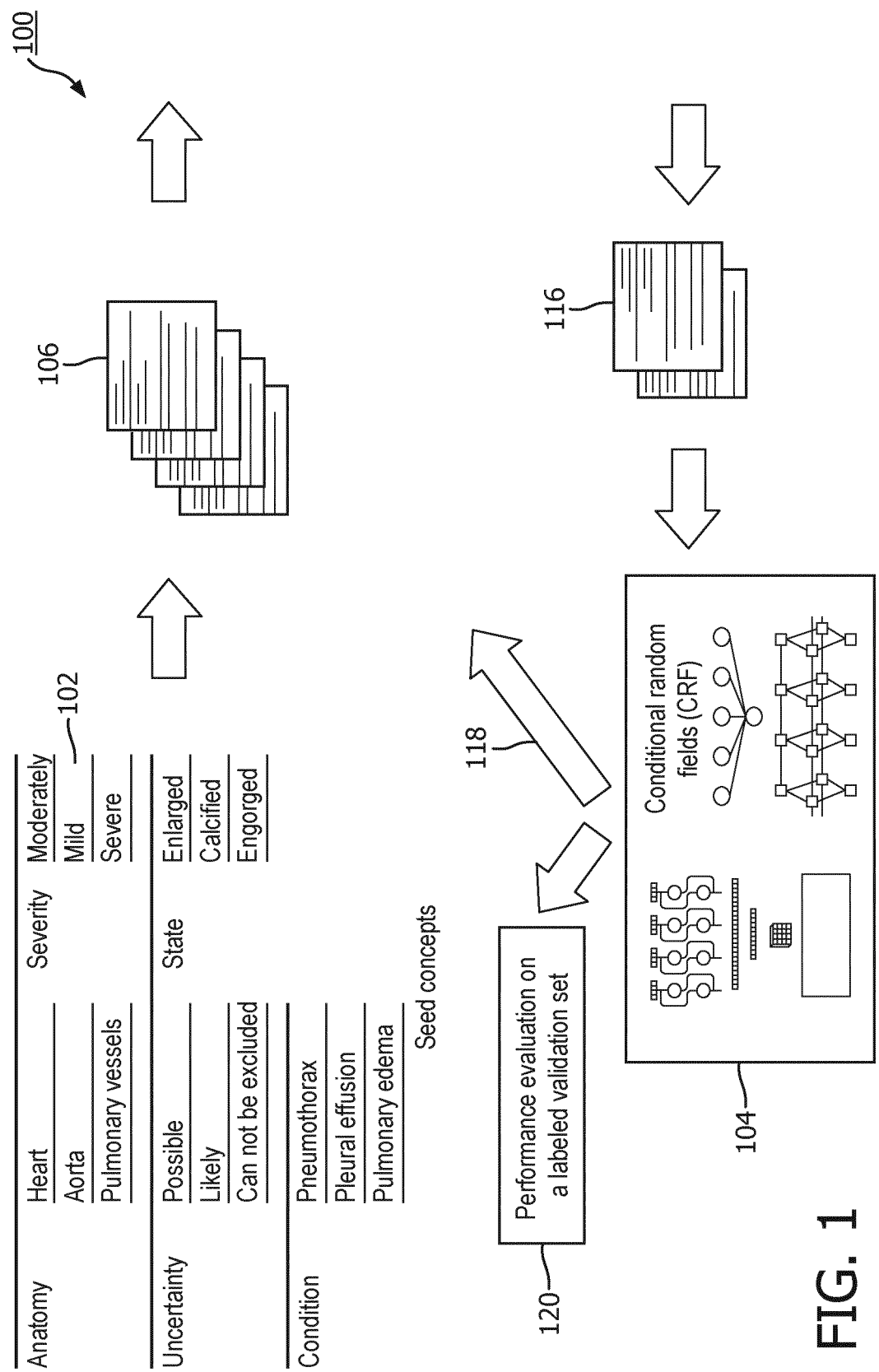
FIG. 1 illustrates a bootstrapping training system 100 that implements a weakly supervised bootstrapping framework that may be used to extract concepts from medical texts.
Figure 1:
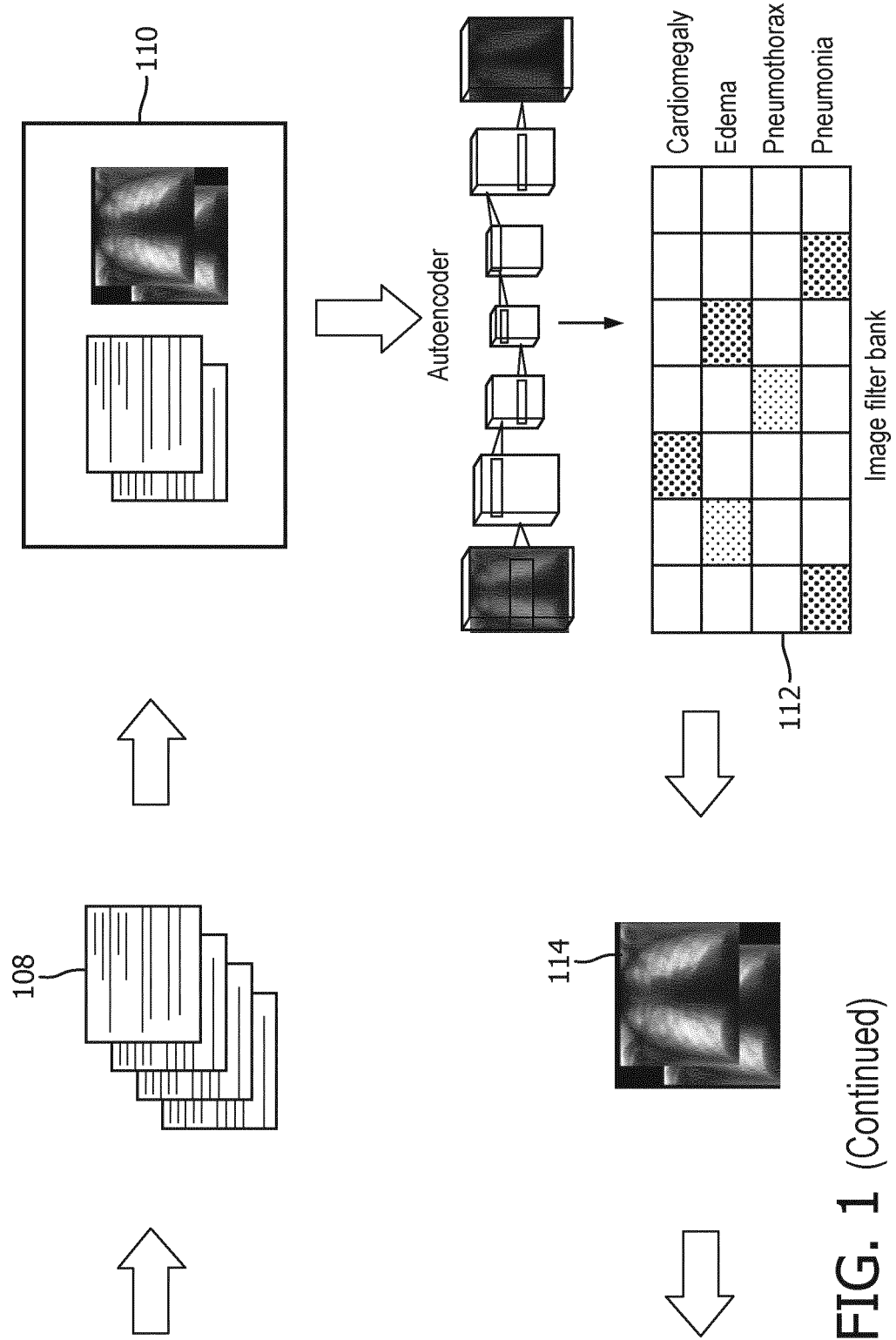

FIG. 1 illustrates a bootstrapping training system 100 that implements a weakly supervised bootstrapping framework that may be used to extract concepts from medical texts such as clinical notes that are often associated with images such as X-ray, MRI or ultrasound images. While examples of the bootstrapping training system is described herein using medical images, such as X-ray, MRI, ultrasound, etc., and their associated medical reports, other images with associated descriptions may be included. Such examples could be images and associated text found in catalogs, instruction and installations manuals, books, product web sites, social media web sites, news web sites, etc. While the bootstrapping training system described herein may be used to train a text identification model for use in classifying text reports in such situations.

The bootstrapping training system will start with a seed dictionary 102 including a small collection of seed concepts that are not ambiguous in different contexts of the text data. This seed dictionary 102 may be formed by a collection of medical concept words and phrases in each category that are the least ambiguous in different contexts of the clinical notes The bootstrapping system will iteratively expand the training instances with the following steps.

The seed dictionary 102 will be used to initially generate a collection of labeled training instances 108 by matching the concept phrases of the seed dictionary 102 in a set of unlabeled data 106. The labeled training instances 108 may be expected to contain some noisy training instances. The number of these initial training instances may be a small number of the available unlabeled training data and may be anywhere from 1% to 10% of the unlabeled data.

With the initial labeled training data, for a given target concept, the accompanying images of the text documents will be extracted to form a set of images associated with the target concept 110. This is easily done as there is at least one image associated with each of the initially labeled reports 108. If there are multiple images associated with a report, all of the accompanying images will be extracted for inclusion in the images set for the concept.

Next, the bootstrapping training system 100 uses image processing algorithms 112 that given a set of clinical images associated with a target medical concept can validate those images with the associated text reports to produce a validated set of representative images 114 for the target medical concept with less noisy or fewer outlier training instances. The labeled reports 116 associated with the validated images 114 are used as a training set for text identification model 104.

The text identification model 104 may be a text classifier that uses various textual data features and a machine learning algorithm suitable for sequence labeling. Example machine learning algorithms may include conditional random field (CRF) classifier, bidirectional long short-term memory (BiLSTM) networks, BiLSTM-CRF, etc. The performance of the text identification model 104 is then determined 120 using a labeled validation set of data.

In the next iteration of the bootstrapping training system 100, unlabeled text reports 106 are input into the text identification model 104 to generate the next set of labeled reports 108, and the system 100 then proceeds to validate those labeled text reports using their associated images as described above. These newly classified instances will act as supplemental training data to retrain the text identification model. The above steps will be repeated until no new reports or images can be identified from the unlabeled data to supplement the labeled training data or when concept extraction performance starts degrading on the validation data set. This image-based approach will aim to reduce the presence of noisy instances in the training data, so that the noise to sample size ratio will be lower.

Figure 2:
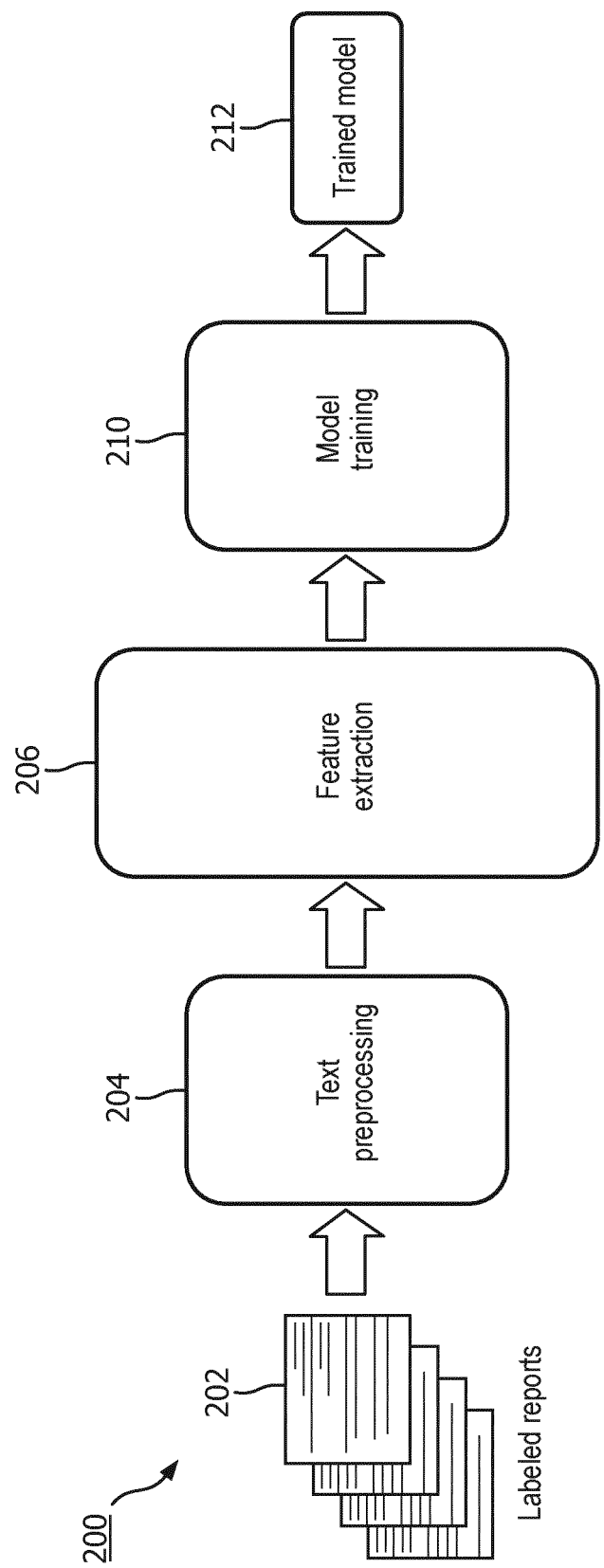
FIG. 2 shows a flow diagram illustrating the training of the text identification model.

FIG. 2 shows a flow diagram illustrating the training 200 of the text identification model 104. The labeled reports 202, which are the same as the set of validated labeled reports 116 of FIG. 1, first undergo text preprocessing 204. The text pre-processing 204 may include tokenization, lemmatization, case normalization, stopwords removal processing, etc. This text pre-processing 204 takes in the raw text of the labeled reports and processes them into a consistent format in order to facilitate feature extraction. Next, the preprocessed text undergoes feature extraction 206. Feature extraction may include looking at each current word in the context of prior words and next words. Also, context words may be identified. Various types of features may be extracted including morphological, orthographic, lexical, and syntactic features. The feature extraction is used to provide inputs into the text identification model 212. Such features need to be defined in a consistent matter so that model may be trained to generate a consistent known set of extracted concepts out of the text identification model 212. It is noted that this text preprocessing 204 and feature extraction 206 may also be used along with the seed dictionary 102 to produce the initial set of labeled training instances 108 produced in the first iteration of the bootstrapping training system described above.

The table below gives examples of feature names, followed by example text, and the resulting feature value. For example, the first four entries use the example text of Cardiomegaly with the following feature names: Word/Phrase, Lowercase, 1 Character suffix, and 2 Character suffix. The associated values are: Cardiomegaly, cardiomegaly, y, and ly. Many other text feature examples are further demonstrated.

| Feature Name | Example Text | Feature Value |
|---|---|---|
| Word/Phrase | Cardiomegaly | Cardiomegaly |
| Lowercase | Cardiomegaly | cardiomegaly |
| 1 Character suffix | Cardiomegaly | y |
| 2 Character suffix | Cardiomegaly | ly |
| If text is uppercase | SVC | True |
| If text is title | Superior Vena Cava | True |
| If text is a digit | 4 | True |
| Lemma form | Increased, increasing, increases | increase |
| Coarse-grained position of speech (POS) | Increased | VERB |
| Fine-grained POS | Increased | VBN (Verb, past participle) |
| Syntactic relation | shift of the trachea | ROOT prep det pobj |
| Syntactic parent | shift of the trachea | Shift shift trachea of |
| Orthographic shape | 77F, 2.2 cm | ddX, d.d xx |
| If text is alphabetic | Cardiomegaly, 77F | True, False |
| If text is a stop word | shift of the trachea | False True True False |
| Left edge | shift of the trachea | shift of the the |
| Right edge | shift of the trachea | trachea trachea the trachea |
| If text is a punctuation | ? | True |
| If text starts sentence | Sternal wires are unremarkable. | True False False False False |

Once the features have been extracted for each of the labeled reports 202, these are used to train 210 the machine learning model to produce the text identification model 212. This may correspond to the generating the text identification model 104 using labeled reports 104 of FIG. 1.

Figure 3:
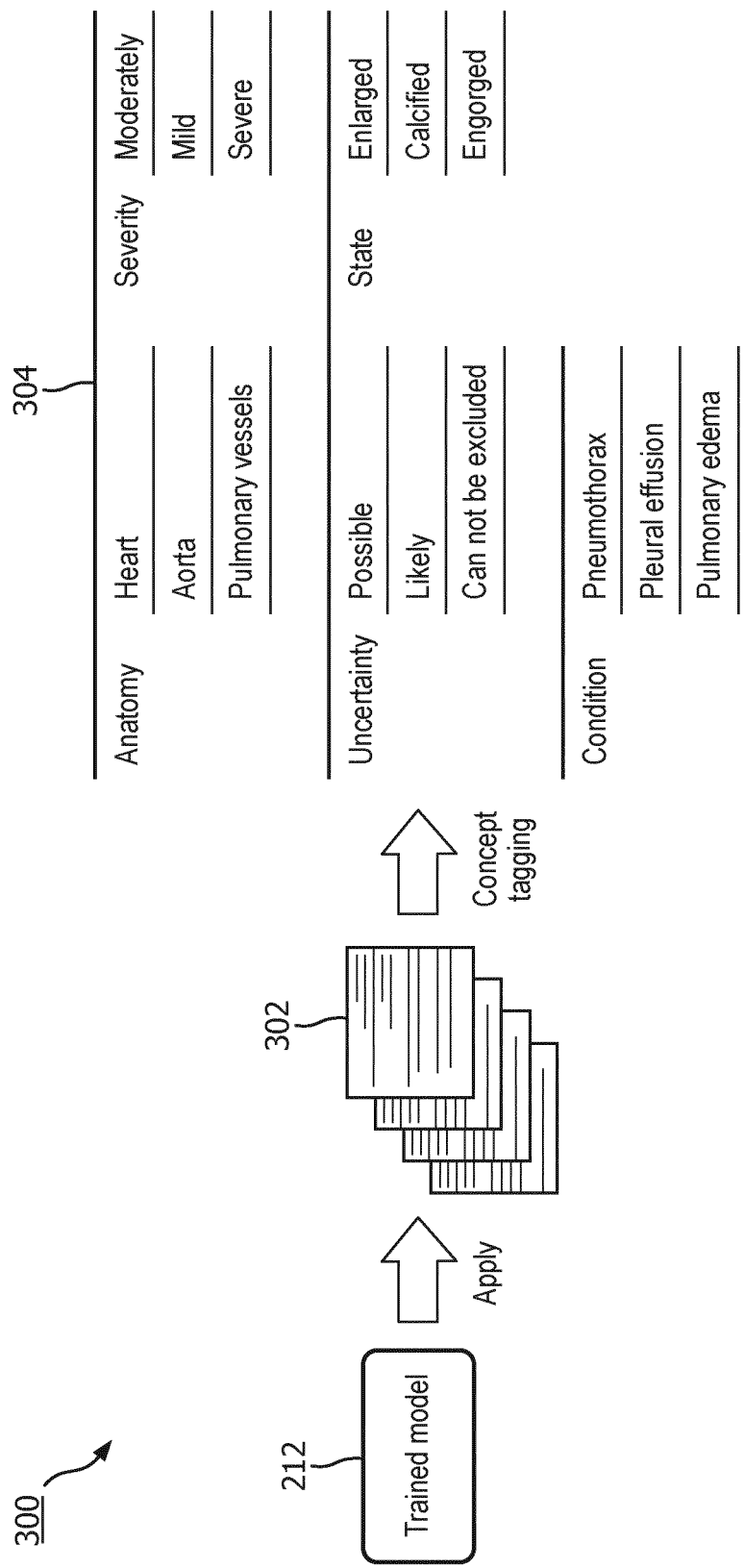
FIG. 3 illustrates the use of the trained text identification model on a set of input unlabeled text reports to produce a set of labels based upon a set of extracted concepts.

FIG. 3 illustrates the use of the trained text identification model 212 on a set of input unlabeled text reports to produce a set of labels based upon a set of extracted concepts 304. This may correspond to step 118 from FIG. 1. In this example, a large number of unlabeled text reports 302 may be input into the text identification model 212 to produce outputs of concepts identified in the unlabeled reports 302. These are the concepts that may be used to label the associated unlabeled images 106 to produce labeled images 108.

Figure 4:
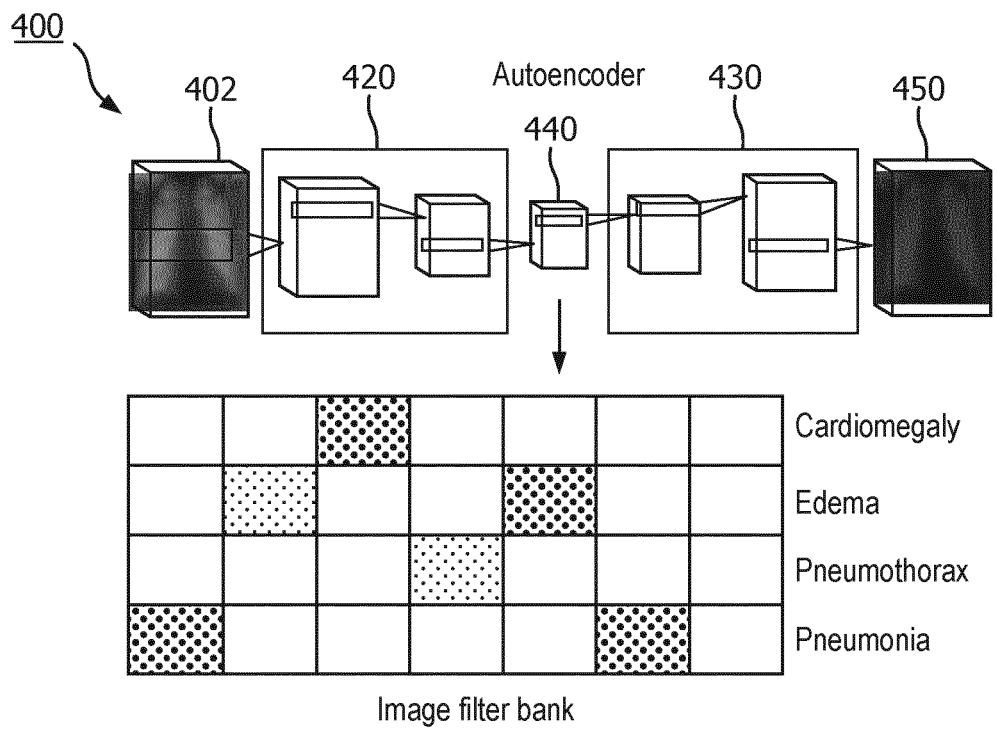
FIG. 4 illustrates an image auto-encoder that maximizes correlation with concepts identified in text reports.

The image processing algorithms 112 used so select validated images 114 will now be described in greater detail. FIG. 4 illustrates an image auto-encoder 400. The auto-encoder 400 includes an encoder 420 and decoder 430. The auto-encoder 400 receives an input image 402 and encodes the input image 402 into an encoded image 440. This encoded image 440 defines the input image in a reduced feature space. The encoded image 440 is then input to the decoder 430 to recreate the original image 450. The auto-encoder 400 is trained using a training data set. The training uses a loss model that compares the output image 450 with the input image 402, with the goals to minimize the difference between the output image 450 and the input image 402.

The bootstrapping training system takes advantage of the fact that encoded image 440 identifies features of the image that may correspond to text features used to describe that image that will be found in the text reports associated with the images. Thus, an image auto-encoder will be used in the filtering process to reduce the noisy text documents, where the auto-encoder will be trained to maximize the correlation of image features with textual features to be used. This correlation will be a correlation matrix. During training with the autoencoder, as the images are encoded to generate representations in a reduced feature space, they are further aligned with corresponding text concepts from the accompanying text documents. The alignment is achieved by generating the dot products of the vector representation of the encoded images with the vector representation of the text concepts from the associated text documents. This is illustrated with a 2D matrix in FIG. 4 named Image Filter Bank. The rows of the matrix represent various text concepts that are mentioned in the text documents and the columns of the matrix represent different images that are input to the auto-encoder. Each cell in the matrix illustrates the correlation of the images with the various concepts. This auto-encoder does not need labeled data to train. It first maximizes the regression of correlation of features using mini-batch optimization. The model converges when the correlation can no longer be increased. The model does not learn perfect correlation between image latent features and language features due to the noise in the data. This correlation matrix that results when the correlation can no longer be increased may be used as a filter bank.

If the concepts found in the text reports can be correlated with the same features found in the associated images, then there will be a high confidence that the text labels applied to the text report are correct. In situations, where there is little correction between the concepts found in the text reports and the associated images, then it is likely that the text labels for the text report are noisy. Such noisy reports may be rejected for use as training samples of the text identification model. When the correlation between the features found in the text labels of the text reports with the features found in the encoded image reaches a threshold value, then such images will be "validated" and may be included in the training set for the text identification model. This may be accomplished as follows.

Assume a set of images, $I \in \mathbb{R}^{B \times N}$, where B is the number of images and N is the dimension of the number of features in the images I. Next, assume a set of text report features, $T \in \mathbb{R}^{B \times M}$, where B is the number of text reports and M is the dimension of the number of features in the text reports I. The auto encoder takes the input image I (402) and encodes it into encoded image I' (440), which is then decoded into output image $\hat{I}$ (450). The goal is the auto encoder is to have the output image $\hat{I}$ be as close as possible to input image I. Further, $I' \in \mathbb{R}^{B \times N'}$, where N'≪N, which indicates that the encoded image has a much reduced feature dimensionality and hence retains the most prominent features of the input image I.

The auto-encoder may be trained using the following loss function:

$$J = MSE - \lambda I'^T \cdot T,$$

where J is the loss function, $MSE = [\hat{I} - I]$ is the mean square error, $\lambda$ is a hyperparameter, and $I'^T \cdot T$ is a correlation matrix.

It is noted that while the mean square error may be used to compare the input image I to the output image $\hat{I}$, other statistical comparisons may be used as well. The goal in training the auto-encoder is to minimize the loss J. Accordingly, when the output image $\hat{I}$ is close to the input image I the MSE is small which minimizes J. Further, when the correlation matrix $I'^T \cdot T$ is large, the features in the text report align closely with the features in the image. As a result the loss J is reduced. Conversely, when the features of the text report do not align with the features in the image, then the loss J is increased. Finally, the hyperparameter $\lambda$ balances the effects of the MSE and the correlation matrix on the loss and is selected as part of training the auto-encoder.

Once the auto-encoder is trained, images 110 associated with the labeled reports 108 are fed into the auto-encoder, that is during inference. The correlation matrix $I'^T \cdot T$ will be used to select which images and associated labeled text reports are used in training the text identification model 104. During inference the imperfect training of the auto-encoder is taken advantage of in order to filter out those text reports which are furthest from the filter bank values. This distance of the given feature and filter bank is the Euclidean Norm. A threshold distance will be used in the selection of valid images that will be tuned on a collection of labeled validation data.

The bootstrapping training system has a plurality benefits in training a text identification system using unlabeled data having associated images. The bootstrapping training system refines noisy training instances to drive weakly supervised bootstrapped learning. Also, the bootstrapping training system improves supplemental training instance selection process in iterative learning. The bootstrapping training system takes advantage of instance validation/sampling with a different data modality (i.e., image-based associated with a text report). The bootstrapping training system does not require labeled image data to train supervised image classification algorithms. Finally, the bootstrapping training system is more robust in preventing propagation of error through iterations because of the instance refinement/validation step.

While the bootstrapping training system is described herein using medical images, such as X-ray, MRI, ultrasound, etc., and their associated medical reports, other images with associated descriptions may be included. Such examples could be images and associated text found in catalogs, instruction and installations manuals, books, product web sites, social media web sites, news web sites, etc. The bootstrapping training system described herein may be used on a text identification model for use in classifying text reports. As described above, an iterative process may be used to select text reports from a set of unlabeled text reports using related images to train the text identification model.

Figure 5:
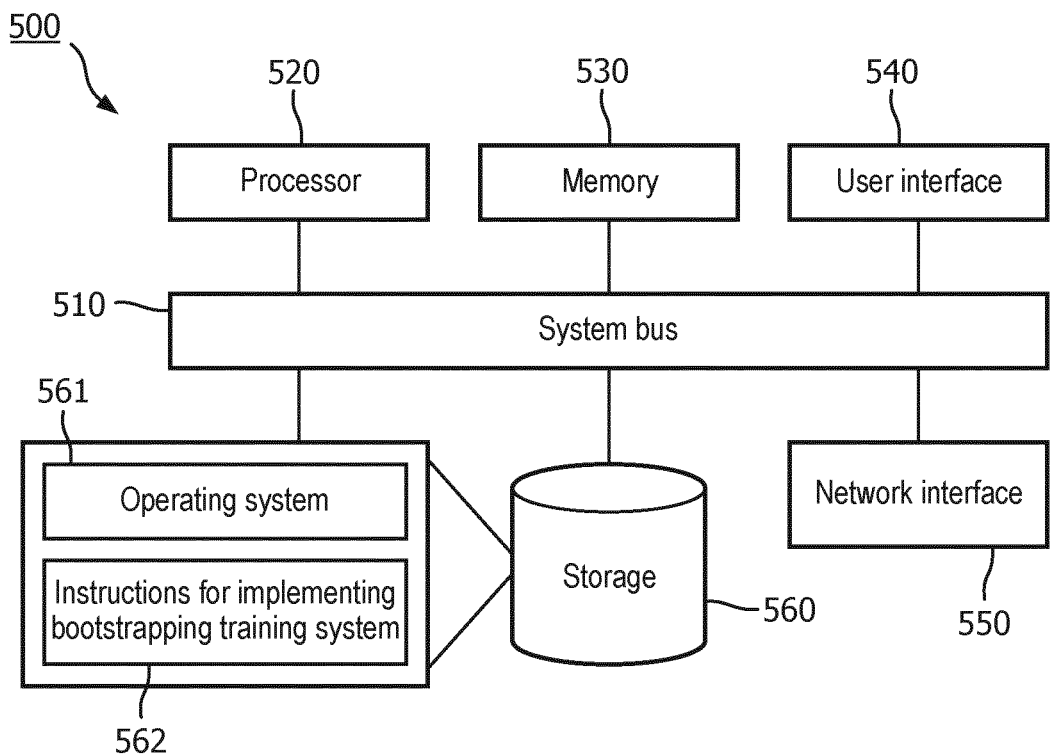
FIG. 5 illustrates an exemplary hardware diagram for implementing the bootstrapping training system.

FIG. 5 illustrates an exemplary hardware diagram 500 for implementing the bootstrapping training system. As shown, the device 500 includes a processor 520, memory 530, user interface 540, network interface 550, and storage 560 interconnected via one or more system buses 510. It will be understood that FIG. 5 constitutes, in some respects, an abstraction and that the actual organization of the components of the device 500 may be more complex than illustrated.

The processor 520 may be any hardware device capable of executing instructions stored in memory 530 or storage 560 or otherwise processing data. As such, the processor may include a microprocessor, a graphics processing unit (GPU), field programmable gate array (FPGA), application-specific integrated circuit (ASIC), any processor capable of parallel computing, or other similar devices.

The memory 530 may include various memories such as, for example L1, L2, or L3 cache or system memory. As such, the memory 530 may include static random-access memory (SRAM), dynamic RAM (DRAM), flash memory, read only memory (ROM), or other similar memory devices.

The user interface 540 may include one or more devices for enabling communication with a user and may present information such. For example, the user interface 540 may include a display, a touch interface, a mouse, and/or a keyboard for receiving user commands. In some embodiments, the user interface 540 may include a command line interface or graphical user interface that may be presented to a remote terminal via the network interface 550.

The network interface 550 may include one or more devices for enabling communication with other hardware devices. For example, the network interface 550 may include a network interface card (NIC) configured to communicate according to the Ethernet protocol or other communications protocols, including wireless protocols. Additionally, the network interface 550 may implement a TCP/IP stack for communication according to the TCP/IP protocols. Various alternative or additional hardware or configurations for the network interface 550 will be apparent.

The storage 560 may include one or more machine-readable storage media such as read-only memory (ROM), random-access memory (RAM), magnetic disk storage media, optical storage media, flash-memory devices, or similar storage media. In various embodiments, the storage 560 may store instructions for execution by the processor 520 or data upon with the processor 520 may operate. For example, the storage 560 may store a base operating system 561 for controlling various basic operations of the hardware 500. The storage 562 may store instructions for implementing the bootstrapping training system described above including training the machine learning model and running the machine learning model on data to be classified.

It will be apparent that various information described as stored in the storage 560 may be additionally or alternatively stored in the memory 530. In this respect, the memory 530 may also be considered to constitute a "storage device" and the storage 560 may be considered a "memory." Various other arrangements will be apparent. Further, the memory 530 and storage 560 may both be considered to be "non-transitory machine-readable media." As used herein, the term "non-transitory" will be understood to exclude transitory signals but to include all forms of storage, including both volatile and non-volatile memories.

While the host device 500 is shown as including one of each described component, the various components may be duplicated in various embodiments. For example, the processor 520 may include multiple microprocessors that are configured to independently execute the methods described herein or are configured to perform steps or subroutines of the methods described herein such that the multiple processors cooperate to achieve the functionality described herein. Such plurality of processors may be of the same or different types. Further, where the device 500 is implemented in a cloud computing system, the various hardware components may belong to separate physical systems. For example, the processor 520 may include a first processor in a first server and a second processor in a second server.

The bootstrapping training system described herein provides many benefits as described above. The bootstrapping training system improves the classification of unlabeled text documents that have associated images that use unsupervised training where text reports with noise labels are filtered out from the training data set. This approach is iterated to increase the size of the training data for the text identification model. This system provides a technical improvement in text identification systems using unsupervised learning when images associated with the text are available.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method for weakly-supervised training of a text report identification machine learning model, comprising:
    labeling a first set of unlabeled text reports based on matching concept phrases of a seed dictionary with concepts in the unlabeled text reports;
    inputting images associated with the first set of labeled text reports into an auto-encoder to obtain an encoded first set of images;
    calculating a set of first correlation matrices as a dot product of the first encoded images with their associated text report features;
    determining a distance between the set of first correlation matrices and a filter bank value associated with the auto-encoder;
    identifying a first set of validated images as the images in the first set of images that have a distance less than a threshold value; and
    training the text report machine learning model using the labeled text reports associated with the set of first validated images.

2. The method of claim 1, further comprising
    labeling a second set of unlabeled text reports using trained text report machine learning model;
    inputting images associated with the second set labeled text reports into an auto-encoder to obtain an encoded second set of images;
    calculating a set of second correlation matrices as a dot product of the second encoded images with their associated text report features;
    determining a distance between the set of second correlation matrices and the filter bank value associated with the auto-encoder;
    identifying a second set of validated images as the images in the second set of images that have a distance less than a threshold value; and
    training the text report machine learning model using the labeled text reports associated with the first set of validated images and the second set of validated images.

3. The method of claim 2, further comprising repeating the steps of claim 2 with additional sets of unlabeled data.

4. The method of claim 3, further comprising completing training text identification machine learning model when no further unlabeled data is available.

5. The method of claim 3, further comprising determining performance of the text identification model using a validation set of data for each iteration of claim 3.

6. The method of claim 4, further comprising completing training text identification machine learning model when performance between iterations is less than a performance change threshold value.

7. The method of claim 1, further comprising training the auto-encoder using a loss function based upon error between an input and output image of the auto-encoder and correlation matrix.

8. The method of claim 7, wherein the loss function is calculated as:

$$J = MSE - \lambda I'^T \cdot T,$$

where J is the loss function, MSE is mean square error between the input image and the output image of the auto-encoder, $\lambda$ is a hyperparameter, $I'^T \cdot T$ is a correlation matrix, $I'^T$ is a transpose of an encoded image, and T is the text report features.

9. A system for training a text report identification machine learning model and an image identification machine learning model, comprising:
a memory; and
a processor connected to the memory, the processor configured to:
label a first set of unlabeled text reports based on matching concept phrases of a seed dictionary with concepts in the unlabeled text reports;
input images associated with the first set of labeled text reports into an auto-encoder to obtain an encoded first set of images;
calculate a set of first correlation matrices as a dot product of the first encoded images with their associated text report features;
determine a distance between the set of first correlation matrices and a filter bank value associated with the auto-encoder;
identify a first set of validated images as the images in the first set of images that have a distance less than a threshold value; and
train the text report machine learning model using the labeled text reports associated with the set of first validated images.

10. The system of claim 9, wherein the processor is further configured to:
label a second set of unlabeled text reports using trained text report machine learning model;
input images associated with the second set of labeled text reports into an auto-encoder to obtain an encoded second set of images;
calculate a set of second correlation matrices as a dot product of the second encoded images with their associated text report features;
determine a distance between the set of second correlation matrices and the filter bank value associated with the auto-encoder;
identify a second set of validated images as the images in the second set of images that have a distance less than a threshold value; and
train the text report machine learning model using the labeled text reports associated with the first set of validated images and the second set of validated images.

11. The system of claim 10, wherein the processor is further configured to: repeat the steps of claim 10 with additional sets of unlabeled data.

12. The system of claim 11, wherein the processor is further configured to complete training text identification machine learning model when no further unlabeled data is available.

13. The system of claim 11, wherein the processor is further configured to determine performance of the text identification model using a validation set of data for each iteration of claim 11.

14. The system of claim 13, wherein the processor is further configured to complete training text identification machine learning model when performance change between iterations is less than a performance threshold value.

15. The system of claim 9, wherein the processor is further configured to train the auto-encoder using a loss function based upon error between an input and output image of the auto-encoder and a correlation matrix.

16. The system of claim 15, wherein the loss function is calculated as:

$$J = MSE - \lambda I'^T \cdot T,$$

where J is the loss function, MSE is mean square error between the input image and the output image of the auto-encoder, $\lambda$ is a hyperparameter, $I'^T \cdot T$ is a correlation matrix, $I'^T$ is a transpose of an encoded image, and T is the text report features.

* * * * *